US007160314B2

(12) United States Patent
Sgro et al.

(10) Patent No.: US 7,160,314 B2
(45) Date of Patent: Jan. 9, 2007

(54) FASTENER FOR FIXING A PROSTHESIS, AND DEVICE FOR DELIVERING THIS FASTENER

(75) Inventors: Jean-Claude Sgro, Dijon (FR); Michel Therin, Lyons (FR); Francois-Regis Ory, Fontaines Saint Martin (FR); Pierre Bailly, Caluire (FR)

(73) Assignee: Sofradim Production, Trevoux (FR)

( * ) Notice: Subject to any disclaimer, the term of this patent is extended or adjusted under 35 U.S.C. 154(b) by 62 days.

(21) Appl. No.: 10/416,858

(22) PCT Filed: Nov. 20, 2001

(86) PCT No.: PCT/FR01/03650

§ 371 (c)(1),
(2), (4) Date: Jun. 10, 2003

(87) PCT Pub. No.: WO02/41790

PCT Pub. Date: May 30, 2002

(65) Prior Publication Data

US 2005/0004575 A1 Jan. 6, 2005

(30) Foreign Application Priority Data

Nov. 24, 2000 (FR) ................................. 00 15239

(51) Int. Cl.
*A61D 1/00* (2006.01)

(52) U.S. Cl. .................. 606/220; 606/75; 606/139; 606/151; 606/219

(58) Field of Classification Search .................. 606/72, 606/75, 216, 219–224, 139, 142, 151, 60, 606/62, 64, 67, 78
See application file for complete search history.

(56) References Cited

U.S. PATENT DOCUMENTS

| 3,716,058 | A | * | 2/1973 | Tanner, Jr. .................. 606/221 |
| 4,006,747 | A | * | 2/1977 | Kronenthal et al. ........ 606/144 |
| 4,669,473 | A | * | 6/1987 | Richards et al. ............ 606/215 |
| 4,696,300 | A | | 9/1987 | Anderson |
| 5,041,129 | A | * | 8/1991 | Hayhurst et al. ........... 606/232 |

(Continued)

FOREIGN PATENT DOCUMENTS

EP 0 847 727 A1 6/1998

(Continued)

*Primary Examiner*—Michael J. Hayes
*Assistant Examiner*—Michael G. Mendoza
(74) *Attorney, Agent, or Firm*—Carter, DeLuca, Farrell & Schmidt, LLP (57) ABSTRACT

A fastener including at least an element to be anchored in an anatomical support, at least a stop element relative to a planar prosthetic component to be fixed, and a linking rod is characterised in that the linking rod is rectilinear and the junction zones of the anchoring element and the stop element with the linking rod enable the fastener to adopt: a non-stressed stripping configuration; a maximum stress configuration, doubled up on itself, for example in a tubular configuration by complete insertion of the fastener into a tube, and a minimum stress configuration, wherein the respective directions of the stop element and the anchoring element form between them, for example in the same plane, an angle not greater than 90°.

18 Claims, 8 Drawing Sheets

U.S. PATENT DOCUMENTS

| | | |
|---|---|---|
| 5,320,633 A | 6/1994 | Allen et al. |
| 5,439,479 A * | 8/1995 | Shichman et al. .......... 606/220 |
| 6,152,935 A * | 11/2000 | Kammerer et al. ......... 606/144 |
| 6,530,933 B1 * | 3/2003 | Yeung et al. ................ 606/151 |
| 6,626,916 B1 * | 9/2003 | Yeung et al. ................ 606/139 |
| 6,692,506 B1 * | 2/2004 | Ory et al. .................... 606/151 |

FOREIGN PATENT DOCUMENTS

| | | |
|---|---|---|
| FR | 2 773 057 | 7/1999 |
| FR | 2 774 227 | 8/1999 |
| GB | 2 306 110 A | 4/1997 |
| WO | WO 00/40159 | 7/2000 |

* cited by examiner

FASTENER FOR FIXING A PROSTHESIS, AND DEVICE FOR DELIVERING THIS FASTENER

FIELD OF THE INVENTION

The present invention relates to a fastener for fixing a prosthesis, for example of bioabsorbable material, used for fixing a planar prosthetic component in the human body relative to an anatomical support. It also relates to the device for delivering this fastener.

BACKGROUND OF THE INVENTION

According to the present invention, the terms used below in the description and the claims have the following meaning:
  "bioabsorbable material" is understood as a material which is decomposed and/or assimilated by and/or in the human or animal body;
  "anatomical support" is understood as non-mineralized human or animal support tissues.

A prosthesis fastener intended for the repair of a fractured meniscus is known from EP-A-0 847 727. This fastener is made up of at least a first immobilizing bar intended to come into abutment against a meniscus fragment, at least one second immobilizing bar intended to come into abutment against another meniscus fragment, and a curved and elastically deformable linking rod. Said immobilizing bars are connected rigidly to this linking rod in such a way that each of them extends perpendicular in relation to the end of the linking rod to which it is connected.

When the fastener is implanted, the linking rod is deformed toward a rectilinear configuration so that it tends to bring the immobilizing bars closer toward one another and thereby ensures retention of the meniscus fragments pressed against one another.

The fastener according to the above document is suitable for repairing a meniscus but could not be used to fix a planar prosthetic component, for example a parietal reinforcement, to an anatomical support, in particular an abdominal wall. The reason is that this fastener with an elastically deformable linking rod and with immobilizing bars connected rigidly to this linking rod prohibits any insertion of said first immobilizing bar inside a tissue wall, and said elasticity is not adapted to such an anchoring.

Document WO 00/40159 describes a fastener which is also intended to repair a meniscus and which cannot be used to fix a planar prosthetic component to an anatomical support.

Figure 17:
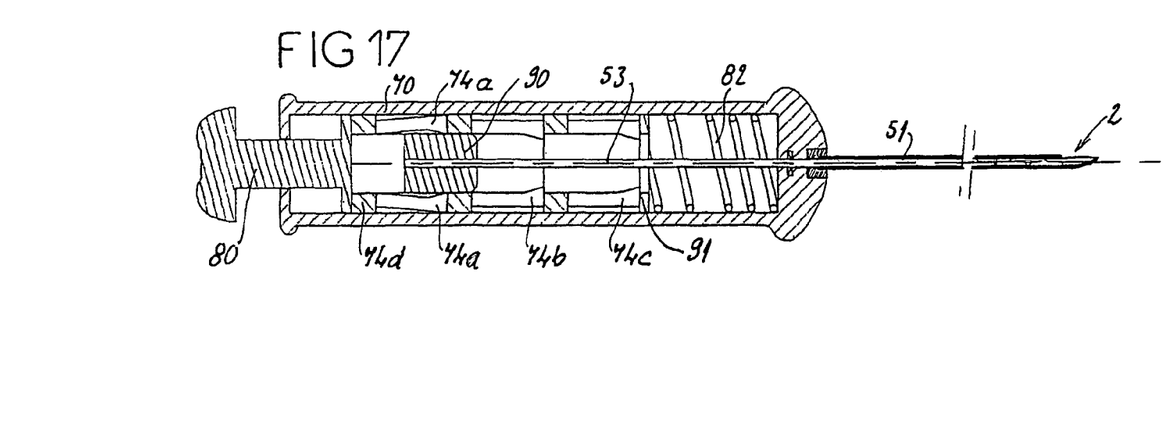

Document US-C-5 203 864 describes an H-shaped fastener intended to fix a planar prosthetic component to an anatomical support (cf. FIG. 17). This fastener comprises:
  a distal element for anchoring in the anatomical support;
  a proximal element for immobilization relative to the prosthetic component; and
  a linking rod, which at one end connects to the distal anchoring element, at an intermediate point on the latter, and at the other end connects to the proximal immobilizing element, at an intermediate point on the latter.

The main disadvantage of the fastener according to said prior art document and of the device for delivering it is that they do not ensure intimate contact of the prosthetic component with the anatomical support, and intimate contact of this kind is, of course, fundamental for good tissue integration of said prosthetic component. The reason is that the distal anchoring element is deployed at a depth determined by the abutment of the proximal immobilizing element against the prosthetic component. However, given the shape of the fastener, this deployment generates a certain retreat of the distal anchoring element relative to this depth, resulting in the aforementioned lack of intimate contact. Moreover, the presence of the linking rod at the end of the distal anchoring element constitutes an obstacle to insertion of this distal anchoring element and can cause a certain amount of damage at the anchoring site, the consequence of which is to affect not only the depth of implantation of the distal anchoring element but also the strength of the anchoring obtained. This, too, may result in said lack of intimate contact.

The present invention aims to provide a solution to this fundamental shortcoming.

SUMMARY OF THE INVENTION

The fastener to which the invention relates has, in a manner known per se, a single-piece structure which can be obtained by molding of a plastics material, for example a bioabsorbable material, and is composed of at least one element for anchoring in an anatomical support, at least one element for immobilization relative to a planar prosthetic component to be fixed, and a linking rod arranged between a zone of connection to the anchoring element and a zone of connection to the immobilizing element.

According to the invention, the linking rod is rectilinear and the zones of connection of the anchoring element and of the immobilizing element to this linking rod allow the fastener to adopt at least three distinct configurations, namely:
  a non-stressed mold-release configuration in which the respective directions of the immobilizing element and of the anchoring element form between them, for example in the same plane comprising the linking rod, an internal angle of at least 90°;
  a configuration of maximum stress, doubled back on itself, for example tubular, by complete insertion of said fastener into a tube, in which configuration the anchoring element and the immobilizing element are folded toward the linking rod and toward one another, as it were end-to-end; and
  a configuration of minimum stress in which the respective directions of the immobilizing element and of the anchoring element form between them, for example in the same plane, an angle not greater than 90°.

The fastener according to the invention permits a surgical approach totally different than that used traditionally. The traditional approach, as is described in document US-C-5 203 884, consists in accessing the posterior face of a tissue wall, from the inside of an anatomical cavity, and in fixing the fastener or fasteners required for holding or fixing the planar prosthetic component.

By virtue of the invention, the fastener can be inserted completely into said tube, with said immobilizing element directed toward the distal end of this tube and said anchoring element directed toward the proximal end of this tube. The latter forms a hollow implantation needle which makes it possible, from the direction of the anterior face of the anatomical support, to insert the fastener beyond the prosthetic component situated against the posterior face of this support; a partial extraction of the fastener from the tube makes it possible to release said immobilizing element, which can bear against the prosthetic component, then a return movement of the tube makes it possible to release the rest of the fastener and thus to implant the anchoring element at a depth which ensures intimate contact of the prosthetic component with the anatomical support.

Consequently, according to the invention, the device for delivering the fastener comprises said tube and the fastener mentioned above, the fastener being inserted into this tube with said immobilizing element directed toward the distal end of this tube and said anchoring element directed toward the proximal end of this tube; this tube comprises a pointed distal end having a lateral opening, and it is provided with a means for retention of the anchoring element below a threshold force; the lateral opening is dimensioned in such a way as to allow extraction of said immobilizing element from the tube when the fastener is pushed into the tube in the proximal to distal direction, and the retention means is positioned in such a way that it ensures retention of the anchoring element in the tube when the immobilizing element is thus extracted from the tube; said retention means is such that, below said threshold force, it permits the retreat of the fastener with the tube and that, once the immobilizing element is bearing against the prosthetic component and the prosthetic component is pressed against the anatomical support, it requires an increased traction on the tube in order to release the anchoring element, thereby ensuring that this anchoring element has a depth of anchoring sufficient to guarantee that said prosthetic component is pressed sufficiently against said anatomical support.

Preferably, said configuration of minimum stress of the fastener corresponds substantially to said mold-release configuration of this fastener.

Advantageously, in said configuration of maximum stress, the anchoring element and the immobilizing element are arranged end-to-end, in a continuation of one another, while the linking rod extends parallel to the direction of alignment of the anchoring element and of the immobilizing element, between the two points of connection to, respectively, the anchoring element and immobilizing element.

By virtue of the invention, the surgical procedure required for delivery of a fastener consists simply in moving the fastener in its configuration of maximum stress, for example tubular, forward through the tissue wall, then pulling the same fastener back in order to obtain or recover a non-stressed configuration, anchored in the tissue wall.

The configuration of a fastener according to the invention also makes it possible to limit the angular stress accumulated upon changing from one configuration to the other at the level of the articulation between the linking rod and, respectively, the immobilizing element and the anchoring element.

BRIEF DESCRIPTION OF THE DRAWINGS

The invention will be better understood from the following description in which reference is made to the attached drawing, in which:

FIG. 8 shows an enlarged view of a detail from FIG. 7, FIGS. 9 and 10 show, respectively in the mold-release configuration and in the tubular configuration of maximum stress, another embodiment of a fastener according to the present invention.

DETAILED DESCRIPTION OF THE PREFERRED EMBODIMENTS

Figure 1:
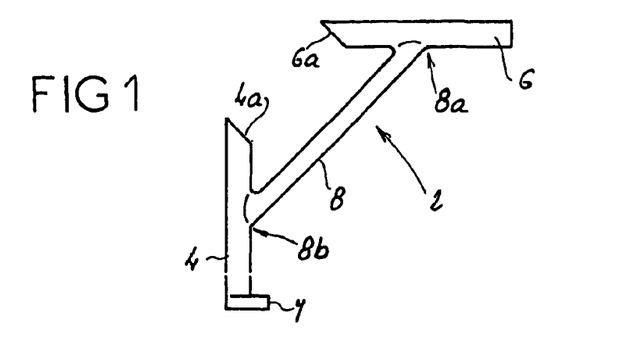
FIG. 1 shows an illustrative embodiment of a fastener according to the invention, in the mold-release configuration.

FIG. 1 shows, in the mold-release configuration, a fastener 2 comprising an anchoring element 4 and an immobilizing element 6 connected via a linking rod 8.

The latter is arranged between an intermediate point of connection 8b to the anchoring element 4 and an intermediate point of connection 8a to the immobilizing element 6.

According to FIG. 2, again in the mold-release configuration, the intermediate rod 8 has a bulge 8c substantially at its center. This bulge 8c consists of an excess thickness of material, of limited length relative to the length of the rod 8, and oriented and disposed only on the top of the core of the rod 8, and inside the fastener 2 in the tubular configuration of maximum stress shown in FIG. 3. As this figure shows, in the tubular configuration the bulge 8c fills or occupies the gap left free between the proximal end of the anchoring element and the distal end of the immobilizing element.

Figure 2:
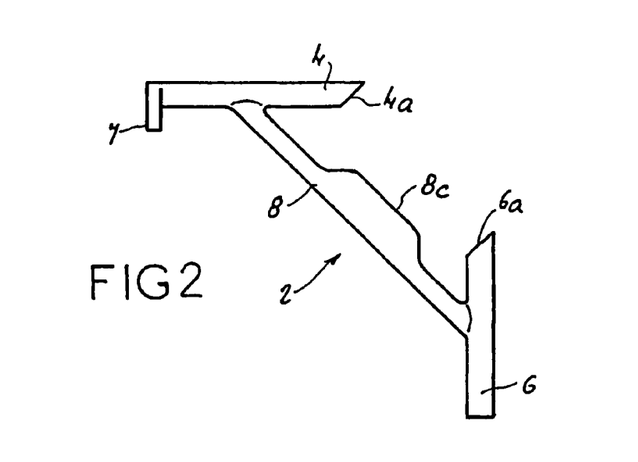
FIGS. 2 and 3 show another illustrative embodiment of a fastener according to the invention, respectively in the mold-release configuration and in the configuration of maximum stress, in tubular shape.

The fasteners 2 shown in FIGS. 1 and 2 have a configuration of minimum stress for retention of a prosthetic component, in which configuration the respective directions of the immobilizing element 6 and of the anchoring element 4 are in the same plane comprising the linking rod 8 and between them form, in said plane, an angle not greater than 90 degrees. In the illustrative embodiments shown in FIGS. 1 and 2, the fasteners which can be obtained by molding are shown in what is called a mold configuration identical to or closely similar to the configuration of minimum stress described above.

Figure 3:
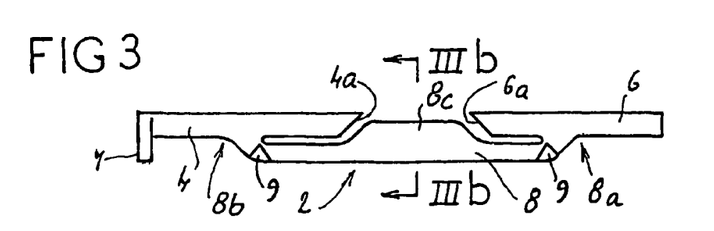
Figure 3B:
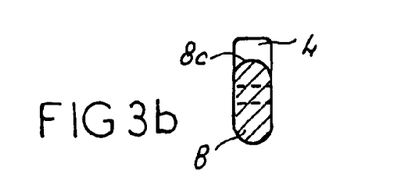
FIG. 3b shows an enlarged cross-sectional view, on the plane IIIb, of the fastener shown in FIG. 3.

FIG. 3 shows a fastener 2 according to the invention in the tubular configuration of maximum stress, as a result of complete insertion of said fastener into a tube (not shown). In this configuration, the anchoring element 4 and the immobilizing element 6 are arranged end-to-end in a continuation of one another, and in particular on either side of the bulge 8c. In this configuration, the linking rod 8 extends parallel to the direction of alignment of the anchoring element 4 and of the immobilizing element 6, between the two intermediate points of connection 8b, 8a to the anchoring element 4 and immobilizing element 6, respectively.

Those ends of the anchoring element 4 and of the immobilizing element 6 which are adjacent in the tubular, stressed configuration compromises two points or bevels 4a, 6a, respectively.

Figure 4:
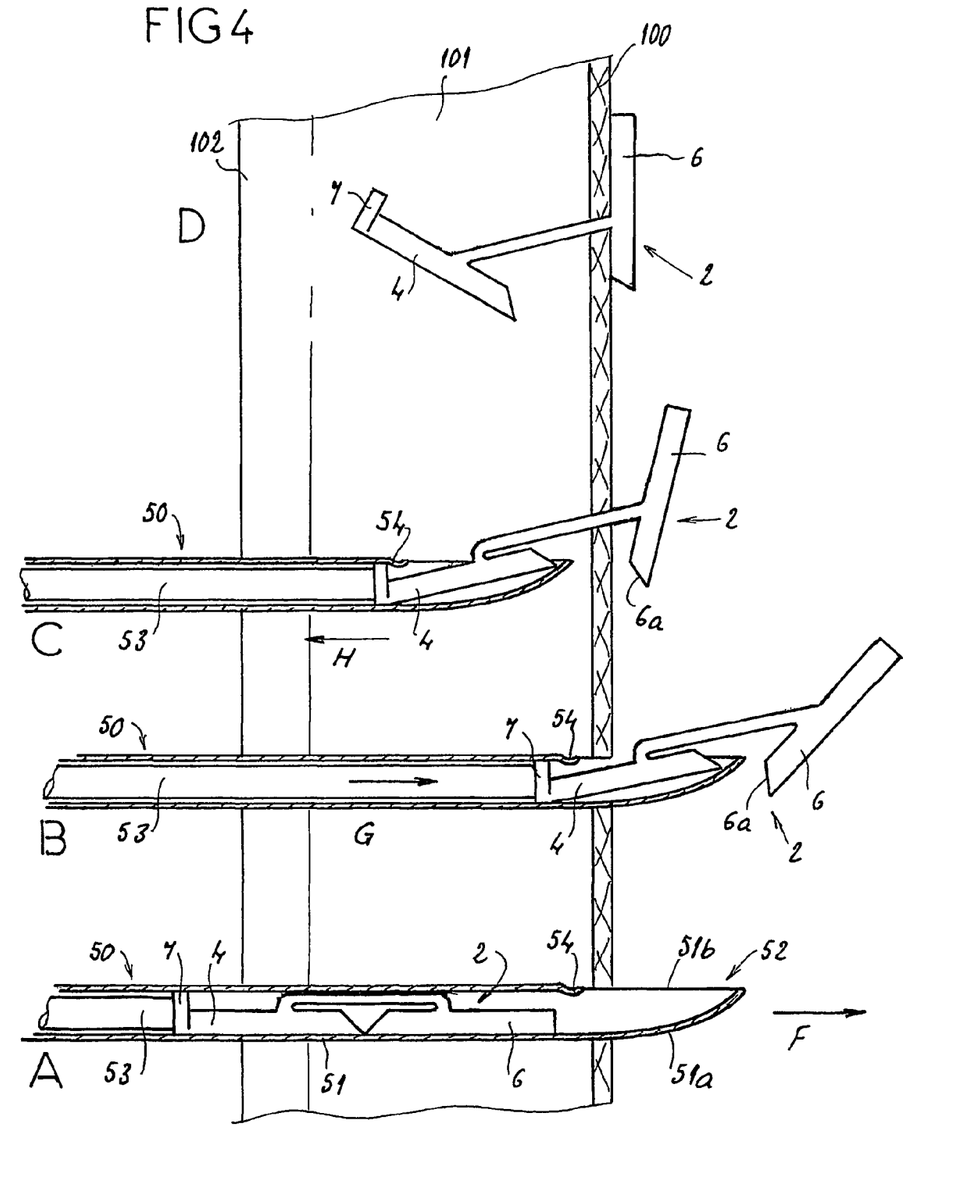
FIG. 4 shows a diagrammatic representation of the method of insertion and delivery of a fastener according to the invention in an anatomical support, FIGS. 5 through 8 relate to another embodiment of a fastener according to the invention, FIG. 5 showing a front view of the fastener in the configuration of maximum stress, FIG. 6 showing a plan view of the fastener in the mold-release configuration, and FIG. 7 showing a side view in the same configuration.
Figure 5:
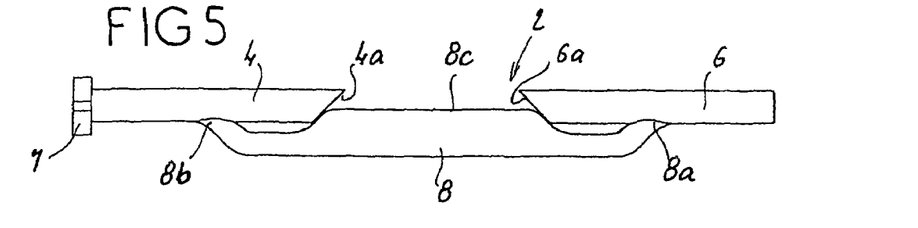
Figure 6:
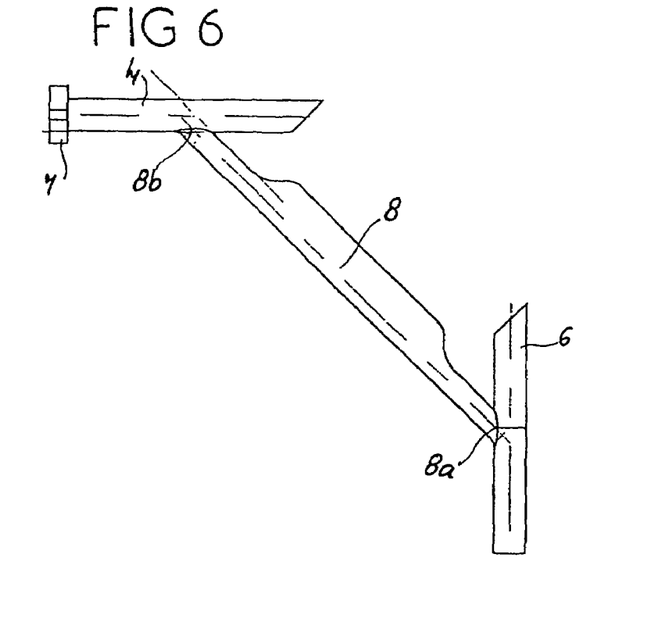
Figure 7:
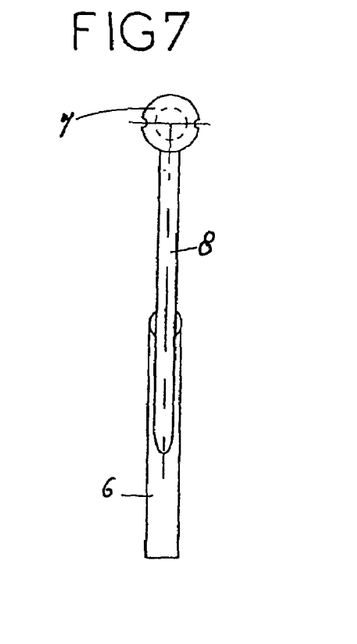
Figure 8:
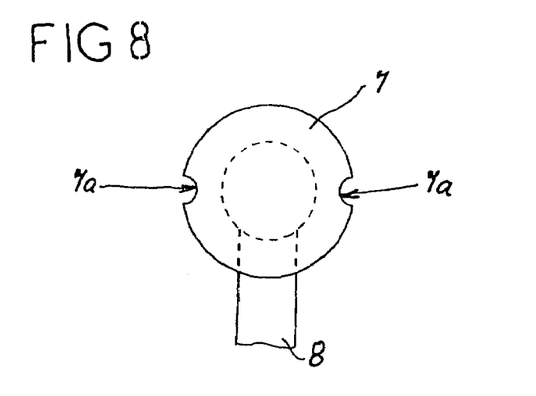

In the tubular configuration of maximum stress, as is shown directly by FIG. 4 (bottom view), or indirectly by FIG. 3, the points or bevels 4a, 6a form an acute angle directed away from the linking rod 8.

In the illustrative embodiment shown in the tubular configuration of maximum stress, in FIG. 3, the two adjacent ends of the anchoring element 4 and of the immobilizing element 6 remain at a distance from one another. The anchoring element 4 and the immobilizing element 6 have substantially the same length, while each intermediate point of connection 8a, 8b is situated substantially at the center of the distal anchoring element 4 or of the immobilizing element 6.

As is shown in particular by FIGS. 9 through 12, the connection of the anchoring element 4 and/or of the immobilizing element 6 to the linking rod 8 can be situated at one end or at a point other than the geometric center of said anchoring element and/or said immobilizing element.

According to the embodiment shown in FIG. 3, two gussets 9 are formed on the linking rod 8 on the outside or opposite the two intermediate points of connection 8a and 8b to the anchoring element 4 and immobilizing element 6, respectively.

The anchoring element 4 comprises, for example, a pusher head 7 arranged at the proximal end of said rod in the tubular stressed configuration.

As is shown in FIG. 4, a fastener 2 according to the invention is inserted through a tissue or muscle wall 101 by means of an insertion device, designated generally by reference number 50, comprising a hollow needle 51. This needle having the form of a Hubert needle comprises an open and pointed distal end 52; more precisely, the tip of the needle 51 is closed by a concave and pointed endpiece 51a, and it comprises a lateral opening 51b opening out in line with the concave endpiece 51a. The distal portion of the needle 51, which serves to perforate then pass through the tissue wall and is continuous and solid outside the opening 51b, on this side of the distal end 52, makes it possible to contain at least one fastener 2 in its tubular configuration of maximum stress. As is shown by FIG. 4, the needle 51 comprises a means 54 of retention (by rearward traction) of the fastener 2. This means 54 consists of one or more stubs obtained by deformation of material, arresting the retention head provided also for this purpose. This retention means is designed in such a way as to permit relative clearance (between itself and the fastener 2 or its head 7), solely by rearward traction on the fastener 2.

The stub or stubs can be arranged relative to the head 7, or vice versa, so as to orient the staple at an angle relative to its axis, in the tubular configuration.

A pusher mandrel 53 is contained inside the needle 50 and is designed to slide freely inside the latter, with distal bearing against the fastener 2 in its tubular configuration of maximum stress, and more precisely its retention head 7. The pusher mandrel 53 comprises a proximal and external end (not shown in FIG. 4) for directly controlling its forward translation by pushing.

FIG. 4 shows an example of the delivery of a fastener according to the invention and more particularly the phases of release of a fastener 2 and fixing of a prosthetic component 100, which consists principally of a prosthetic tissue, in the surgical procedure employed in the context of the present invention.

This fixing is performed on an anatomical support 101 consisting of a tissue or muscle wall.

A fastener of this kind is delivered by being passed through the tissue using the transcutaneous insertion device 50, which is passed through the skin 102 of the patient from outside the body.

The fastener 2 thus makes it possible to fix the prosthetic component 100 as is shown at phase D in FIG. 4.

During a first phase A, described below, the needle 51 passes through the skin 102, then the tissue wall, and also the prosthetic component 100, in such a way as to be able to release the immobilizing element 6 beyond and in front of said prosthetic component 100, by way of the open and pointed distal end 52, starting from the tubular configuration of maximum stress shown in FIG. 4A.

The method for delivering the fasteners 2 according to the invention is set out for example in FIG. 4 and can be divided into four phases, A, B, C, and D.

During the first phase (phase A), the insertion device allows the needle 51 to be introduced through the skin 102, the tissue wall 101 and the prosthetic component 100. The needle 51 passes through the prosthetic component 100 by a distance sufficient to allow the open and pointed distal end 52 to release the immobilizing element 6, by pushing with the mandrel 53 in the direction of arrow G during phase B, which element moves at least partially away from its stressed, tubular configuration after its release. The pusher mandrel 53 displaces the fastener 2 until the beveled end 6a emerges from the needle 51.

According to phase C in FIG. 4, the operating surgeon exerts a rearward traction on the insertion device 50 and, consequently, on the needle 51 in the direction of arrow H in order to draw the immobilizing element 6 back against the prosthetic component 100. From this moment, the fastener 2 changes toward its configuration of minimum stress in which it is relatively open. The immobilizing element 6 thus departs substantially from its stressed, tubular position in such a way as to extend substantially in a direction perpendicular to that of the linking rod 8.

As is shown under C in FIG. 4, the beveled shape 6a of the end of the immobilizing rod 6 directed toward the prosthetic component 100 makes it possible, by rearward traction of the fastener 2 (of which a part remains inside the needle 51) to tilt the rod 6 into a position in which it is flat or parallel to the component 100 or wall 101.

Thereafter, an additional rearward traction exerted on the needle 51 makes it possible to clear the retention means 54, for example by deformation or by flexion of the pusher head 7 of the fastener 2, which is then released from the needle 51. The fastener 2 is then in the relatively open configuration of minimum stress, shown diagrammatically at phase D in FIG. 4. In this configuration, the proximal anchoring element 4 also departs reasonably substantially from its position in the mold configuration of the fastener and anchors in the wall 101.

The points or bevels 6a and 4a, respectively, of the immobilizing element 6 and of the anchoring element 4 contribute to excellent insertion of said fastener 2 in any anatomical support in which the proximal rod 4 lodges.

It is not necessary for the anchoring element 4 to unfold completely to assume an angular direction perpendicular to that of the linking rod 8 in order to ensure holding or fixing of the prosthetic tissue 100 on the anatomical support. A slight departure of the anchoring element 4 from its relative position in the stressed tubular configuration of the fastener suffices.

The presence of the bulge 8*c* makes it possible to lengthen the rod 8 without thereby weakening it with respect to the longitudinal forces which its receives, both during pushing for insertion and delivery of the fastener, in the tubular configuration of maximum stress, and during traction for changing to the configuration of minimum stress for retention of the prosthetic component 100.

The lengthening of the rod 8 makes it possible to increase the depth of anchoring within the thickness of the penetrated tissue wall 101, which increases the thickness of the biological material, for example tissue, serving for retention of the prosthesis by means of the fastener which has been delivered.

The shape used for the bevels 4*a* and 6*a* on the one hand ensures retention of the immobilizing element 6 in the prosthetic component penetrated previously by the fastener 2, by tilting of said bar, forced by rearward traction of the fastener, and on the other hand promotes the anchoring of the rod 4, when the rod 8 is under traction, on account of the transverse movement of the prosthetic component 100, and thus the transverse movement of the immobilizing element 6.

As is shown in FIG. 4, part D, the head 7 serves as a means of immobilizing the anchoring in the tissue wall.

The fastener according to FIGS. 5 through 8 differs from that described with reference to FIG. 1 in that:

- in the tubular configuration of maximum stress, the bevels 4*a* and 6*a* abut against two oblique flanks, respectively, of the bulge 8*c*,
- the head 7 comprises two peripheral notches or grooves permitting passage of a gas, for example a sterilizing gas, when the corresponding fastener is in the stressed configuration and stored inside a needle 51.

Figure 9:
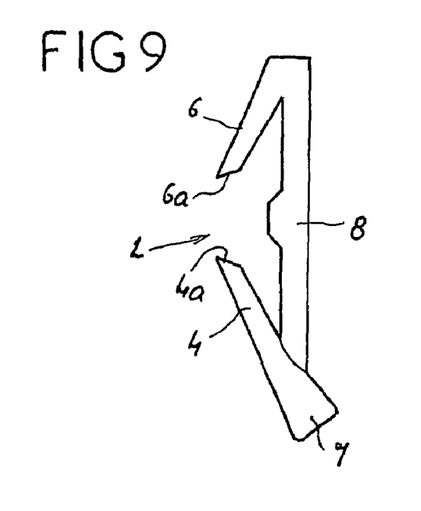
Figure 10:
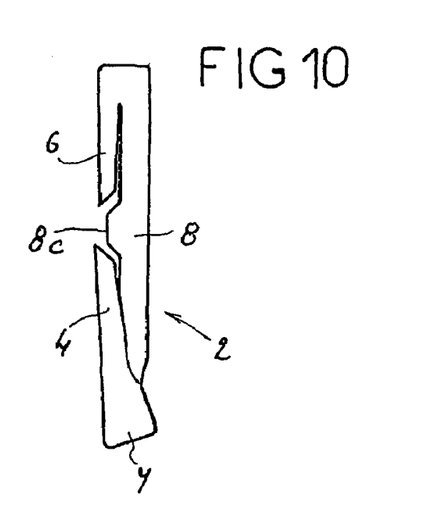

The fastener 2 according to FIGS. 9 and 10 is characterized on the one hand by an anchoring rod 4 and an immobilizing element 6 with a cross section which decreases in the direction away from the linking rod 8, and on the other hand by an immobilizing element 6 articulated at its non-free end on the linking rod 8.

Figure 11:
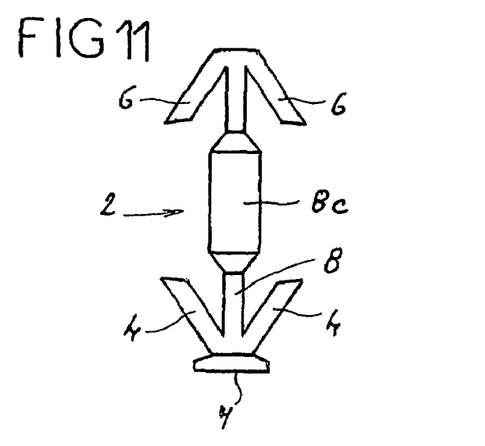
FIGS. 11 and 12 show, respectively in the mold-release configuration and in the configuration of maximum stress, another embodiment of a fastener according to the present invention.
Figure 12:
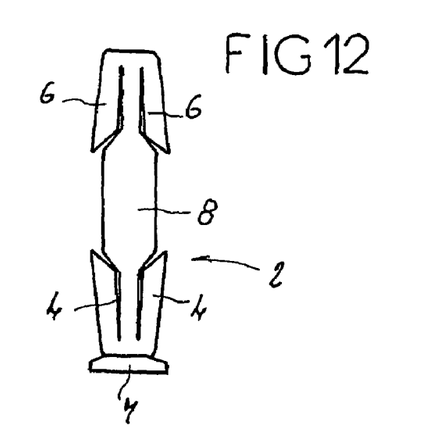

The fastener according to FIGS. 11 and 12 is characterized by several immobilizing bars 6 radiating and several anchoring rods 4 radiating from the two respective ends of the linking rod, the bulge 8*c* having the form of a hub.

Figure 13:
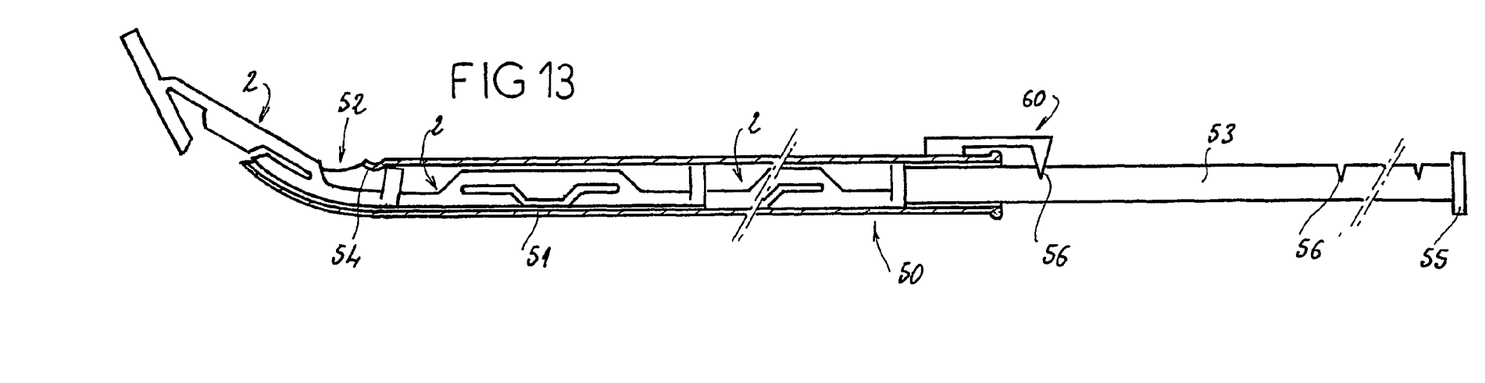
FIG. 13 shows an example of a transcutaneous insertion device according to the invention, for delivering a fastener according to the invention in an anatomical support.
Figure 14:
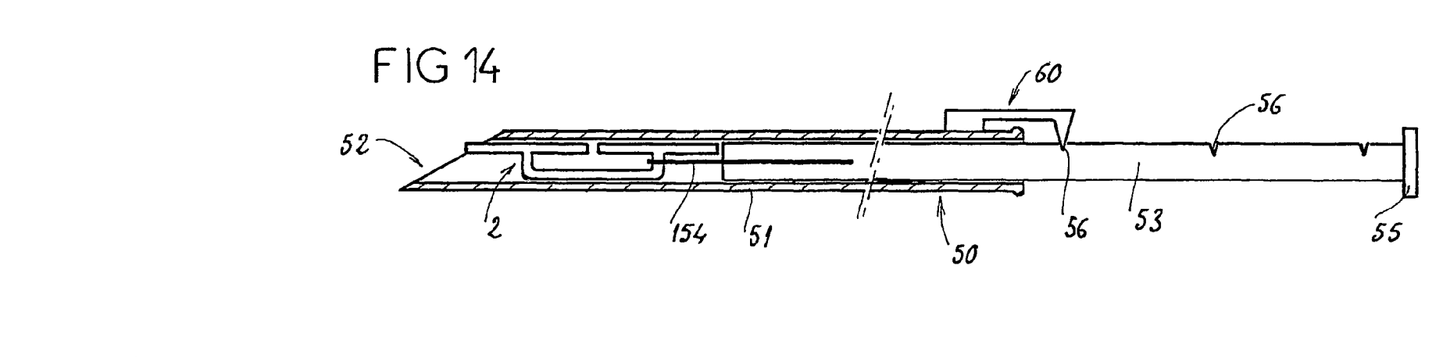
FIG. 14 shows an alternative design of an insertion device according to the invention.
Figure 15:
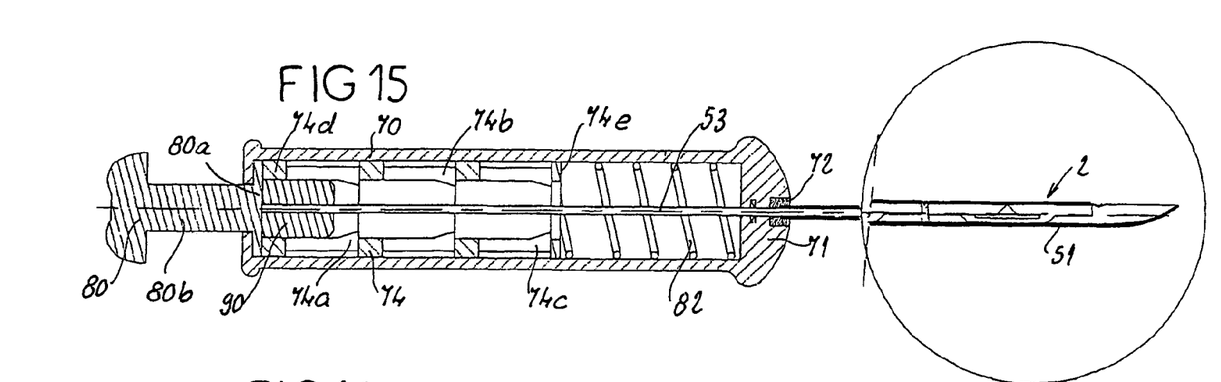
FIGS. 15 through 18 show another example of a transcutaneous insertion device according to the invention, in different phases of functioning.

FIGS. 13 and 14 show two illustrative embodiments of a device for insertion through tissue in accordance with the invention. The transcutaneous insertion device 50 shown in FIG. 13 comprises the needle 51 having the open and pointed distal end 52, and an end in which the pusher mandrel 53 is introduced, at the external and proximal end of which pusher mandrel 53 a control member 55 is arranged.

The distal penetrating portion of the needle 51 comprises a charge or a plurality of fasteners 2 stored end-to-end, each in their tubular configuration of maximum stress inside the hollow needle 51.

The transcutaneous insertion device 50 also comprises a graduated means 60 of registering the advance of the pusher mandrel 53 inside the needle 51, thus indicating to the operating surgeon the number of fasteners 2 used. This means 60 makes it possible to count the number of fasteners 2 released when fixing the prosthetic component 100 on the anatomical support, in this case the tissue wall 101.

The retention means 54 is dimensioned in such a way as to retain the pusher head 7 in a manner sufficient to optimally position the immobilizing element 6 against the prosthetic component 100.

The illustrative embodiment of the insertion device shown in FIG. 14 comprises only a single fastener 2 in the needle 51. Unlike the retention means designated by 54 in FIG. 13, this one designated 154 in FIG. 14 is made with a rod or a wire connecting said fastener 2 to the pusher mandrel 53.

The insertion devices 50 in FIGS. 13 and 14 are disposable, containing just one fastener 2 according to the invention in the embodiment according to FIG. 14 and containing a charge or several fasteners in the embodiment according to FIG. 13.

FIGS. 15 through 19 show another illustrative embodiment of a device for insertion through tissue in accordance with the invention. The insertion device comprises a handle 70, at a distal end 71 of which the needle 51 is mounted coaxially. The needle 51 is mounted on the handle 70 with the aid of an engagement piece 72 integral with the needle 51 and engaged at least partially in said control handle 70. This engagement piece 72 is joined to the distal end 71 of said handle 70 by any known means, in particular by screwing or adhesion.

The pusher mandrel 53 passes coaxially and freely through the needle 51. This pusher mandrel 53 bears at the distal end against a fastener 2 and is arranged at the proximal end freely inside a slide 74 which is mounted freely and in translation, coaxially in the handle 70. At its proximal end, the mandrel is integral with a core or counter-abutment 90 coaxial to the needle 51 and to the mandrel 53.

Along its axis, the slide 74 comprises a series of axial stops 74*a*, 74*b*, 74*c* which are radially elastic outward and are in a number identical, less one, to the number of fasteners 2 arranged in the penetrating distal portion of the needle 51. The axial stops 74*a*, 74*b*, 74*c* are spaced apart along the axis of the slide 74 and are separated by a distance equal to the length of a fastener 2 in its tubular stressed configuration, which determines the basic forward travel of the pusher mandrel 53.

A pusher member 80 emerges for a part 80*b* of the handle 70 and is mounted movably in translation coaxially in the latter, its distal end bearing against the end of the slide 74 remote from the needle 51. The member 80 comprises, inside the handle 70, a distal face 80*a* opposite the emerging part 80*b* bearing against the slide 74 and against the counter-abutment 90 prior to the first use of the insertion device.

This device comprises a means 82 for return of the slide 74 to a rest position, in which the proximal end 74*d* of the slide 74 and the distal face 80*a* of the gripping member 80 bear against one another. The return means 82 is, for example, a spring mounted in the handle 70, specifically between the distal end of the slide 74, via a washer 91, and the distal end 71 of the handle 70.

A non-return means 84 is provided between the distal end 71 of the handle 70 and the pusher mandrel 53. The non-return means 84 permits the movement of said pusher mandrel 53 forward of said handle 70 and blocks its rearward movement, again relative to said handle. The pusher mandrel 53 is thus blocked in translation in each of its basic advance positions, each corresponding to the complete withdrawal of a fastener 2 from the needle 51. Each of these basic positions is embodied by each of the distal face 80*a* and the axial stops 74*a*, 74*b*, 74*c* in the position of return of the slide 74.

Each of the stops 74*a* through 74*c* is designed to escape from the counter-abutment 80 when the pusher mandrel 53 is arrested in translation by the non-return means 84, and when the slide 74 is returned to its return or rest position. For this purpose, each stop 74*a* through 74*c* consists of one or more radially elastic teeth, comprising an inner heel 95 profiled to escape from the counter-abutment 90 when the slide 74 retreats under the action of the spring 82, and to resist the counter-abutment 90 when the slide 74 advances, and so that the frontal and distal face of each elastic tooth bears against the counter-abutment 90.

When the operating surgeon wishes to extract a fastener 2 from the needle 51 with the transcutaneous insertion device described above, he starts from a position shown in FIG. 15. He then presses on the pusher member 80 in order to compress the return means 82 and displace the pusher mandrel 53 by translation so as to expel the immobilizing element 6 from the needle 51. The travel of the member 80 displaces the pusher mandrel 53 so that the pusher head 7 and the retention means 54 come substantially into contact for the first fastener 2 intended to be withdrawn from the needle 51. This then gives the arrangement shown in FIG. 16.

Figure 16:
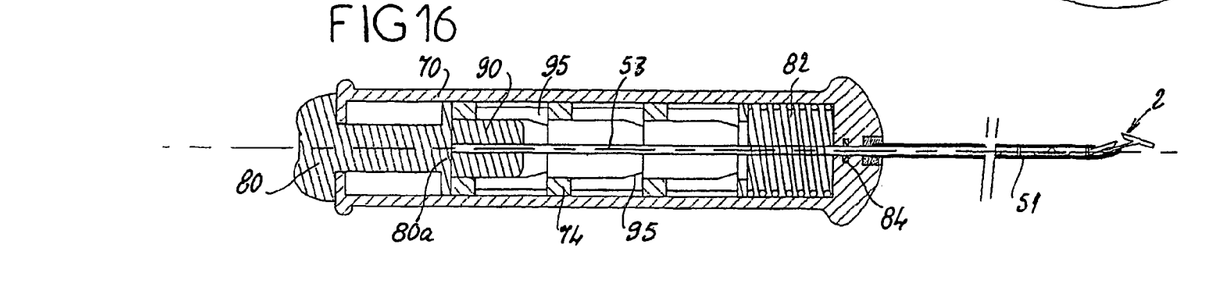

The operating surgeon can then exert a traction on the needle 51 by way of the handle 70 in order to position the fastener 2 against the prosthetic component 100 with the immobilizing element 6, that is to say against the tissue wall 101. Exerting a rearward traction this makes it possible to free the pusher head 7 from the retention means 54.

When the operating surgeon then releases the member 80, the latter returns to its rest position under the action of the return means 82. The displacement of the slide 74 inside the handle 70 is effected without any relative movement between the pusher mandrel 53 and the handle 70, this being by virtue of the non-return means 84.

Figure 18:
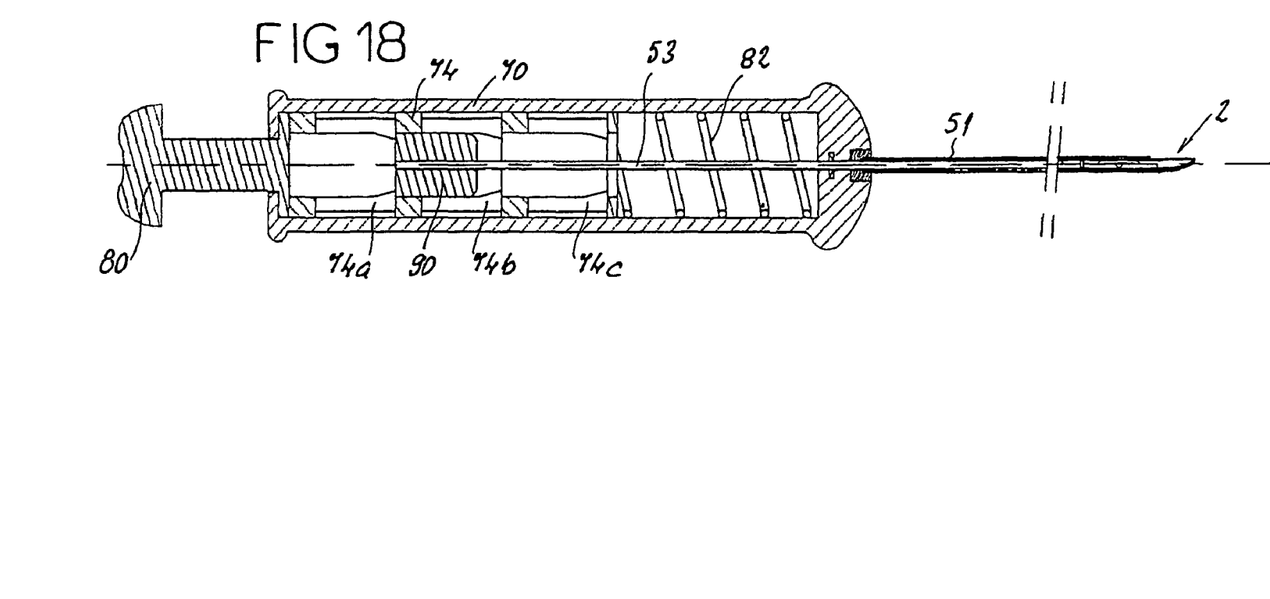
Figure 19:
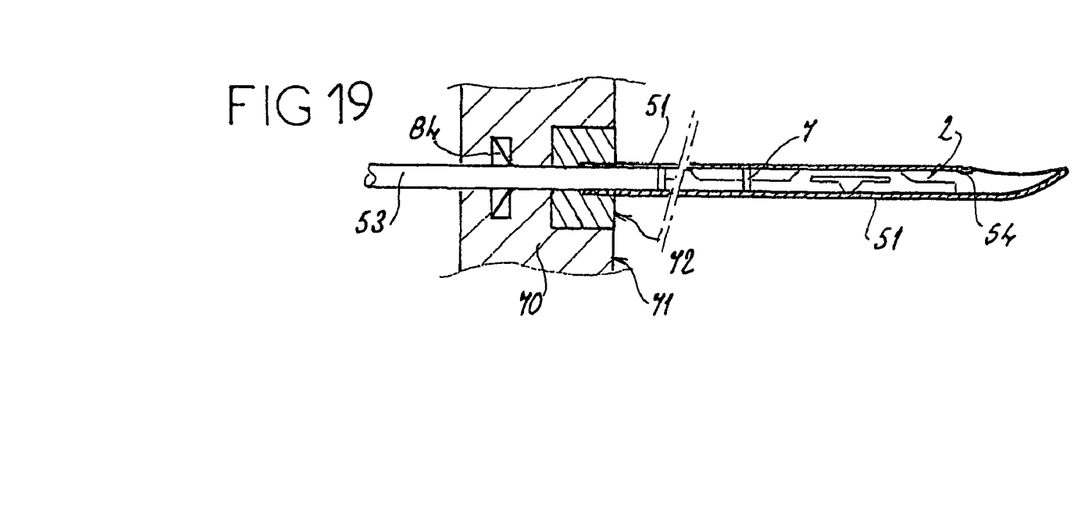
FIG. 19 shows a detail of the device according to FIGS. 15 through 18.
Figure 20:
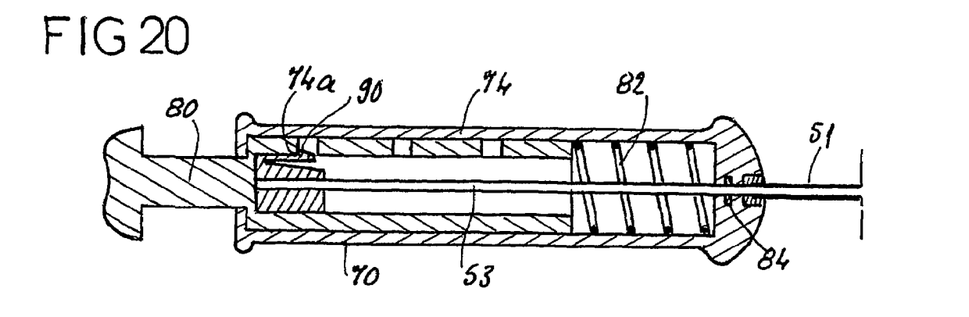
FIGS. 20 through 23 show an alternative version of the insertion device shown in FIGS. 15 through 19, in different phases of functioning.
Figure 21:
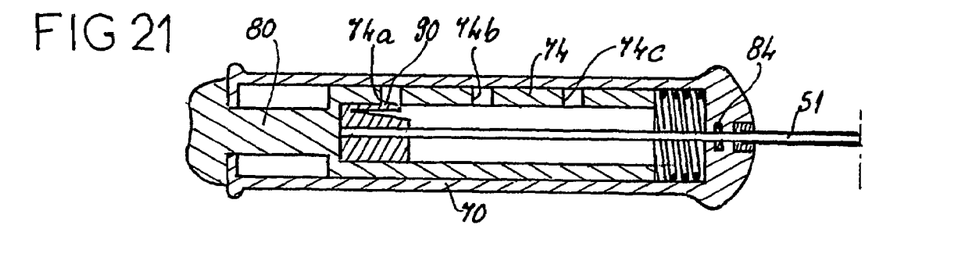
Figure 22:
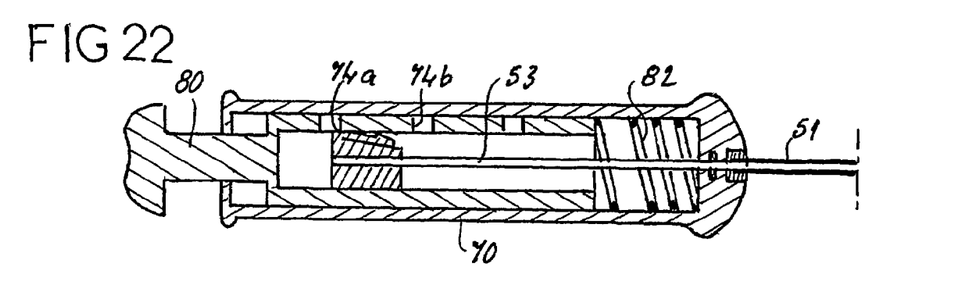
Figure 23:
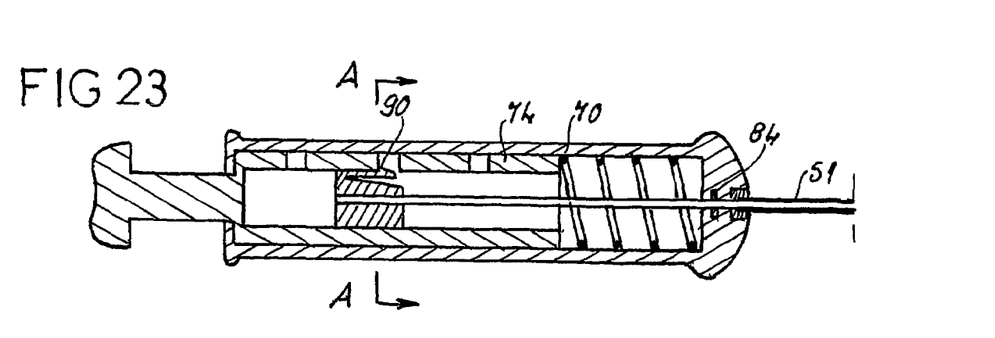
Figure 23B:
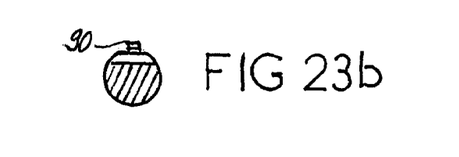
FIG. 23b shows a cross section, on the line A—A in FIG. 23, of a detail of said alternative version.

The counter-abutment 90 then comes to lodge in front of the first stop 74*a* provided inside the slide 74, as is shown successively in FIGS. 17 and 18. It is in this new position that the counter-abutment 90 will lodge at the second stop 74*b* and will bear against the first stop 74*a* in the event of a further advance of the pusher member 80.

The insertion device is then in a standby position shown in FIG. 18.

According to the surgical delivery method described in FIG. 4, when the fastener 2 is fully extracted from the needle 51, the insertion device shown in FIGS. 15 through 18 is then in an arrangement in which it is possible to extract a second fastener 2. This is because, when the gripping member 80 is pushed, the slide 74 displaces the pusher mandrel 53 by translation via the first axial stop 74*a* to a second basic position situated in front of and past the position of the second axial stop 74*b* when the slide 74 is at rest. Thus, when the immobilizing element 6 of the second fastener 2 is expelled from the needle 51, and the pusher head 7 of the second fastener 2 comes into contact with the retention means 54, the operating surgeon releases the member 80, which under the effect of a return means 82 places the slide 74 once again in its rest position. The counter-abutment 90 will then lodge in front of the second axial stop 74*b*. The complete release of the second fastener 2 can be obtained in this way, and an additional fastener, in this case a third fastener 2, will then be able to be extracted from the needle 51, and so on. The insertion device according to the invention and shown in FIGS. 15 through 19 is not limited to an example permitting the delivery of four fasteners 2. On the contrary, the corresponding needle 51 can comprise charges with different numbers of fasteners. The size of the insertion device and the diameter of the corresponding needle can also vary without departing from the scope of the present invention. By way of example, the needle 51 can have an internal diameter of 1.6 mm.

The device shown in FIGS. 21 through 23 and 23*b* differs from the device described above in the following ways:

instead of constituting a separate component of the slide 74, the pusher member 80 is integral with or forms a single piece with the slide, to escape from the counter-abutment 90, when the slide 74 retreats toward its rest position, on the one hand each axial stop 74*a*, 74*b*, 74*c* belonging to the slide 74 is formed by a catch which consists of a through-hole (circular slit for example) in the wall of the hollow slide 74, and, on the other hand, the counter-abutment 90 is formed by one or more teeth which are able to deform elastically radially outward, such a tooth having a flat surface abutting against the aforementioned catch, in the direction of pushing of the member 80, and a bevel for sliding against the inner face of the slide 74, in the opposite direction.

The invention claimed is:

1. A fastener that can be delivered through a tube for fixing a planar prosthetic component to an anatomical support, comprising: a single-piece structure that can be obtained by molding of a plastics material, and having at least one anchoring element adapted to engage the anatomical support, at least one immobilizing element that engages the planar prosthetic component to be fixed, and a linking rod that flexibly engages a zone of connection of the anchoring element located in approximately a middle of a length of the anchoring element and that flexibly engages a zone of connection of the immobilizing element located in approximately a middle of a length of the immobilizing element and the linking rod having a bulge located in the center of the linking rod separating an end that engages the zone of connection of the anchoring element and an end that engages the zone of connection of the immobilizing element; the linking rod being rectilinear and the zones of connection allowing the fastener to adopt at least three distinct configurations:

a non-stressed mold-release configuration in which respective directions of an axis of the immobilizing element and of an axis of the anchoring element form between them, in the same plane having an axis of the linking rod, an internal angle of at least 90°;

a configuration of maximum stress, doubled back on itself, by complete insertion of said fastener into the tube, in which the configurations of the anchoring element and the immobilizing element are folded toward the linking rod and toward one another; and are arranged end-to-end, and the linking rod axis extends parallel to the direction of the anchoring element axis and the immobilizing element axis, and a configuration of minimum stress in which the respective axes of the immobilizing element and the anchoring element form between them, in the same plane, an angle not greater than 90°.

2. The fastener as claimed in claim 1, wherein the configuration of minimum stress corresponds substantially to the mold-release configuration.

3. The fastener as claimed in claim 1, wherein an end of the anchoring element and an end of the immobilizing element are adjacent in the configuration of maximum stress, each end having bevels.

4. The fastener as claimed in claim 3, wherein, in the configuration of maximum stress, the bevels form an internal angle.

5. The fastener as claimed in claim 1, wherein at least one gusset is formed on the bulge of the linking rod.

6. The fastener as claimed in claim 3, wherein, in the configuration of maximum stress, the adjacent ends of the anchoring element and the immobilizing element remain at a distance from one another.

7. The fastener as claimed in claim 1, wherein the anchoring element has a retention head arranged at a proximal end of the anchoring element in the tubular stressed configuration.

8. The fastener as claimed in claim 1, wherein the anchoring element and the immobilizing element have substantially the same length, while each point of connection to the linking rod is situated substantially at the center of the anchoring element or immobilizing element.

9. A device for delivering a fastener in combination with the fastener as claimed in claim 1, wherein the tube is adapted to permit the fastener to be inserted into the tube with said immobilizing element directed toward a distal end of the tube and said anchoring element directed toward a proximal end of the tube; the tube having a pointed distal end having a lateral opening, and provided with a means for retention of the anchoring element below a threshold force during delivery; the lateral opening adapted to allow extraction of said immobilizing element from the tube during delivery when the fastener is pushed into the tube in the proximal to distal direction, and the retention means is adapted to retain the anchoring element in the tube when the immobilizing element is extracted from the tube during delivery; said retention means also adapted to permit the retreat of the fastener with the tube during delivery and said retention means also adapted to, once the immobilizing element is bearing against the prosthetic component and the prosthetic component is pressed against the anatomical support during delivery, require an increase traction on the tube to release the anchoring element from the retention means so that the completion of delivery, the anchoring element has a depth of anchoring sufficient to fix said prosthetic component to said anatomical support.

10. The combination as claimed in claim 9, wherein the a distal penetrating portion of the tube is continuous so as to completely contain at least one said fastener in its stressed tubular configuration.

11. The combination as claimed in claim 9, wherein the distal penetrating portion of the tube holds a plurality of fasteners arranged end-to-end, each in their stressed tubular configuration.

12. The combination as claimed in claim 9, wherein the device further comprises a pusher mandrel that engages the proximal end of a fastener arranged in its stressed tubular configuration in the distal penetrating portion of the tube, said pusher mandrel being designed to penetrate into and move freely inside the tube, and having a proximal and external end.

13. The combination as claimed in claim 12, wherein the external and proximal ends of the pusher mandrel has a control member.

14. The combination as claimed in claim 9, wherein the distal penetrating portion holds a plurality of fasteners arranged end-to-end, each in their stressed tubular configuration.

15. The combination as claimed in claim 12, wherein the device further comprises a graduated means for registering the advance of the pusher mandrel inside the tube.

16. The combination as claimed in claim 12, wherein the device further comprises:

a handle on which the tube is mounted coaxially, at a distal end of said handle;

a slide mounted freely in translation, coaxially inside said handle, said slide having a series of axial stops which are in identical number, less one, to a number of fasteners held in the distal penetrating portion of the tube and which are distributed and separated along an axis of the handle by a same distance corresponding to a basic forward travel of the pusher mandrel;

a pusher member emerging from said handle and mounted so as to be movable in translation inside said handle, on the other side of the slide in relation to the tube;

a means for returning the slide to a rest or return position in which the proximal end of the slide and the distal end of a gripping member are in abutment against one another;

a pusher mandrel arranged coaxially, at inside the distal end of the tube, and integral at the proximal end with a counter-abutment; and a non-return means between the handle and the pusher mandrel for allowing said mandrel to move in translation forward of said handle and blocking its rearward movement, in relation to said handle, each of the axial stops of the slide being arranged to escape from said counter-abutment when, with the mandrel blocked in translation by the non-return means, the slide is drawn back to a rest position.

17. The combination as claimed in claim 16, wherein the pusher member is separate from the slide or forms a single piece together with said slide.

18. The combination as claimed in claim 16, wherein in order to escape from the counter abutment, each axial stop is made up of one or more radially outwardly elastic teeth, or each axial stop is formed by a catch and the counter-abutment is formed by at least one radially inwardly elastic tooth.

* * * * *